United States Patent [19]

Blount

[11] 4,113,693
[45] Sep. 12, 1978

[54] PROCESS FOR THE PRODUCTION OF ACRYLIC COMPOUNDS AND RESINOUS PRODUCTS

[76] Inventor: David H. Blount, 5450 Lea St., San Diego, Calif. 92105

[21] Appl. No.: 804,897

[22] Filed: Jun. 9, 1977

Related U.S. Application Data

[63] Continuation-in-part of Ser. No. 703,925, Jul. 9, 1976, Pat. No. 4,011,253.

[51] Int. Cl.$^2$ .............................................. C08G 77/04
[52] U.S. Cl. ............................. 528/271; 260/448.2 R; 260/448.8 R; 526/279
[58] Field of Search ................................... 260/46.5 R

[56] References Cited

U.S. PATENT DOCUMENTS 4,011,253   3/1977   Blount ........................ 260/46.5 R X Primary Examiner—Paul F. Shaver

[57] ABSTRACT

A fine granular silica is chemically reacted with an acrylic compound by using a strong alkali catalyst and by heating the mixture. The acrylic silicate compound is then polymerized with a catalyst such as a peroxide initiator.

18 Claims, No Drawings

PROCESS FOR THE PRODUCTION OF ACRYLIC COMPOUNDS AND RESINOUS PRODUCTS

CROSS-REFERENCE TO RELATED COPENDING APPLICATION

This application is a continuation-in-part of U.S. patent application No. Ser. 703,925, filed July 9, 1976 now U.S. Pat. No. 4,011,253.

BACKGROUND OF THE INVENTION

This invention relates to a process for the production of acrylic silicate compounds and resinous products by chemically reacting silica ($SiO_2$) with an acrylic compound to produce an acrylic silicate compound. The acrylic silicate compound may be polymerized with a catalyst such as a peroxide initiator.

The silica compound used in this process may be produced by any of the commonly known processes. It is preferred to be in the form of fine granules of powder. Best results occur when 1 part by weight of fine granular silica is reacted with 1 to 4 parts by weight of the acrylic compounds. In the polymerization process, the acrylic silicate compound apparently also acts as the cross-linking agent.

The acrylic acid compound will react more readily with the silica than the acrylate compounds. The acrylate compounds probably react with the silica by alcoholysis by the use of a strong alkali catalyst. The chemical reaction of silica requires a much stronger alkali catalyst and more heating than that required to react a hydrated silica with an acrylic compound as illustrated in U.S. patent application Ser. No. 703,925, filed July 9, 1976 by David H. Blount.

The exact course of the reactions which take place during the process to produce poly(acrylic silicate) polymers cannot be determined with 100% certainty.

The acrylic silicate compounds may be co-polymerized with other polymerable compounds such as styrene, acrylonitrile vinyl chloride, butadiene, allyl chloride, vinyl acetate, vinylidine chloride, 2-chloroethyl vinyl ether, allyl esters of dicarboxylic acids, allyl ethers of dihydric alcohols, ally alcohol, aliphatic dichlorides, calcium carbide, chlorotrifluoroethylene, divinyl benzenes, propylene oxide, ethylene oxide, vinyl toluenes, N-vinyl carbazole, vinyl pyrolidone, methyl vinyl ketone, aryl vinyl ketones, alkyl vinyl ketones, acrylic aldehyde, methacrylonitrite, vinylidine cyanide, dichlorostyrene, 3-chloropropene, bis (2-chloroethyl) ether and mixtures thereof.

The acrylic silicate resinous products produced in my process may be ground into a powder, softened with heat and then molded into useful products. The acrylic silicate resinous products may be produced with various silicate content so that they are soluble in common solvents such as aqueous ammonium solution, acetic acid, alcohols, dilute sulfuric acid, alkali metal hydroxide solutions, acetone and other organic solvents. The acrylic silicate resinous products may be produced which are insoluble in the common solvents but may be molded into useful products. A solution of the acrylic silicate resinous products may be painted on wood and used as an adhesive or a tough protective coating. The acrylic silicate resinous products may be produced as dispersions in aqueous solutions and may be painted on wood and forms a tough protective coating when dried. The acrylic silicate resinous products may be reacted with calcium hydroxide and used as a soil stabilizer.

SUMMARY OF THE INVENTION

I have discovered that a fine granular silica will react chemically with an acrylic compound in the presence of a strong alkali catalyst to produce an acrylic silicate compound which may be polymerized with a catalyst such as a peroxide initiator. This basic process may be varied to produce products having varied properties. The proportions of silica, catalyst and acrylic compound may be varied, for example, to produce a resinous product ranging from very hard to soft and rubbery.

The acrylic silicate compounds are produced by chemically reacting the silica with an acrylic compound in the presence of a strong alkali catalyst before a polymerizing catalyst is added.

The preferred method of this invention is to mix the silica, alkali catalyst, acrylic compound and peroxide initiator in an aqueous solution then heat the mixture to 80° to 100° C. while agitating until the reaction is substantially complete thereby producing an acrylic silicate resinous product.

The reactants may be mixed in any suitable proportions, depending upon the product characteristics desired. Generally, 1 mol of silica is mixed with 1 to 4 mols of the acrylic compound. A catalytically effective amount of the selected alkali catalyst is used. Generally, depending upon the alkali catalyst selected and the reaction conditions desired, from 0.1 to 1 mol of the alkali catalyst per mol of silica is used.

The reactions of this invention may take place under any suitable physical conditions. While many of the reactions will take place acceptably at ambient temperature and pressures, in some cases, better results may be obtained at somewhat elevated temperatures and pressures. Preferably, the reaction takes place at a temperature between 50° C. and the boiling temperature of the solution. A pH of above 10 is preferred in this process.

Any suitable acrylic compound may be used in this process. Typical acrylic compounds include acrylic acid, methacrylic acid, ethyl acrylic acid, crotonic acid, chloroacrylic acid, fluoroacrylic acid, cyclohexyl acrylic acid, ethyl acrylate, propyl acrylate, butyl acrylate, pentadecyl acrylate, hexadecyl acrylate, benzyl acrylate, cyclohexyl acrylate, phenyl ethyl acrylate, ethyl methacrylate, methyl x-chloroacrylate, 2-chloroethyl acrylate, 1,1-dihydroperfluorobutyl acrylate, lauryl acrylate, cyclohexyl-cyclohexyl methacrylate, allyl methacrylate, methyl methacrylate, cyclohexyl methacrylic acid, ethylene methacrylate, isobutyl methacrylic acid, n-butyl methacrylate, polyethylene glycol dimethacrylate, tetraethylene glycol dimethacrylate and mixtures thereof.

Any suitable alkali catalyst may be used in this process. Various alkali metal hydroxides, oxides, carbonates and alkali metal salts of weak acids may be used. The preferred alkali catalysts are the alkali metal hydroxides such as sodium hydroxide and potassium hydroxide. Best results are obtained when 0.25 to 0.5 parts per weight of the alkali metal hydroxide is used with about 1 part by weight of the silica. The preferred alkaline earth metal hydroxide is calcium hydroxide. Any strong alkali compound may be used as the catalyst such as alkali polysulfides and calcium carbide.

Various peroxide initiators may be used as potassium persulfate, ammonium persulfate, hydrogen peroxide, cumene hydroperoxide, p-menthane hydroperoxide, potassium and ammonium persulfate with ferric sulfate or cupric sulfate, and others. A redox system of initiation may be used. Benzoyl peroxide with a tertiary amine activator, such as N,N-dimethyl aniline may be used. Anionic agents will polymerize acrylic silicate compounds. Organic peroxides and hydroperoxides such as ethyl ketone peroxide with cobalt naphthenate, benzoyl peroxide, acetyl benzoyl peroxide, p-chlorobenzoyl peroxide, alkoxy benzol peroxide, lauroryl peroxide, dibutyryl peroxide, dicaproyl peroxide, crotonyl peroxide, di-tert-alkyl peroxides, methyl amyl ketone peroxide, di-tert butyl diphosphate peroxide, periacetic acid and cyclohexyl hydroperoxide and mixtures thereof.

Any suitable modifying or additive compounds may be used in the reaction of this invention to vary the properties of the resinous product. Typical additives include aliphatic dihalides, maleic anhydride, polyester resins, polyether resins, polyurethane resins, sodium silicate, calcium hydroxide, sulfur, lead oxide, methacrylic anhydride, polysilicic acid esters, hydrated silica, polybutenes, alkylated polystyrenes and mixtures thereof.

Any suitable emulsifier may be used in the reaction of this invention. Typical emulsifiers include sodium alkyl sulfate, soaps of fatty acids (oleic, myristic, palmetric), anionic and cationic emulsifying agents and mixtures thereof.

The primary object of the present invention is to produce acrylic silicate compounds and resinous products. Another object is to produce acrylic silicate compounds that can be copolymerized with unsaturated organic chemicals to form new resins. Still another object is to produce acrylic silicate compounds and resinous products that are readily soluble in aqueous or organic solvents and may be used as a protective coating on wood. Still another object is to produce useful molding powders.

DESCRIPTION OF PREFERRED EMBODIMENTS

My invention will be illustrated in greater detail by the specific examples that follow, it being understood that those preferred embodiments are illustrative of, but not limited to, procedures which may be used in the production of acrylic silicate compounds and resinous products. Parts and percentages are by weight unless otherwise indicated.

EXAMPLE I

About 2 parts by weight of acrylic acid, 1 part by weight of sodium hydroxide flakes, 2 parts by weight of fine granular silica (200 to 325 mesh) and about 10 parts by weight of water are mixed. The mixture is agitated at ambient temperature and pressure for 1 to 10 minutes thereby producing a thick mixture of silica, acrylic silicate and sodium acrylate.

About 10 parts by weight of water are added to the said mixture. To polymerize the mixture, about 0.01 parts by weight of potassium persulfate, and about 0.001 parts by weight of ferric sulfate are added to the said mixture then agitated for 10 to 30 minutes thereby producing an acrylic silicate resinous product, poly(acrylic silicate) polymer. The polymer is coagulated by adding a mineral acid, dilute hydrochloric acid (3N), until the pH is about 5 to 6. The water and salt is filtered off thereby recovering the resinous product. About 0.5 parts by weight of the resinous product was soluble in the hydrochloric acid solution and was precipitated by the addition of sodium carbonate until the pH was about 7 to 8.

About 0.5 parts by weight of the poly(acrylic silicate) polymer was soluble in water and precipitated by the addition of acetic acid until the pH was about 5 to 6. About 1 part by weight was soluble in alcohol and acetic acid. About 1 part by weight of the poly(acrylic silicate) polymer was not soluble in water, acetic acid, alcohol, hydrochloric acid, acrylic acid or alkali metal hydroxides. The unsoluble portion would soften on heating (70° to 100° C.) and can be molded into tough elastic products.

EXAMPLE II

About 2 parts by weight of fine granular silica, 1 part by weight of sodium hydroxide flakes, 2.5 parts by weight of methacrylic acid, and 6 parts by weight of water are mixed then agitated at ambient pressure and temperature for 1 to 10 minutes thereby producing a thick mixture of silica, methacrylic silicate and sodium methacrylate.

The mixture is then polymerized by adding 10 parts by weight of water, about 0.01 to 0.02 parts by weight of potassium persulfate, and about 0.001 to 0.002 parts by weight of cupric sulfate then agitating for 10 to 30 minutes thereby producing an acrylic silicate resinous product, poly(methacrylic silicate) polymer.

The poly(methacylic silicate) polymer is coagulated by adding an acid, dilute hydrochloric acid, until the pH is about 5 to 6. The water and sodium chloride is filtered off.

The poly(methacrylic silicate) polymer is soluble in isopropyl alcohol. About 0.5 parts by weight of silica are unreacted with the methacrylic acid.

EXAMPLE III

About 2 parts by weight of fine granular silica, 1.5 parts by weight of sodium hydroxide flakes, 3 parts by weight of methyl methacrylate and 10 parts by weight of water are mixed then agitated at ambient temperature and pressure for about 1 to 10 minutes thereby producing a thick mixture of silica, methyl methacrylate silicate and sodium methacrylate.

The mixture is then polymerized by adding about 10 parts by weight of water, about 0.01 to 0.02 parts by weight of potassium persulfate and about 0.001 to 0.002 parts by weight of ferric sulfate then agitated for 10 to 30 minutes at ambient temperature; the reaction is complete in 2 to 12 hours thereby producing an acrylic silicate resinous product.

The methyl methacrylate silicate emulsion is coagulated by dilute hydrochloric acid until the pH is about 7 to 8. The white resinous product is soluble in acetone and isopropyl alcohol. About 1 part by weight of the silica was unreacted with the methyl methacrylate.

The solution of methyl methacylate silicate may be painted on wood and forms a tough clear protective coating when dried.

EXAMPLE IV

About 2 parts by weight of silica (200 to 325 mesh), 1 part by weight of sodium hydroxide flakes, 3 parts by weight of methyl methacrylate, 10 parts by weight of water, 0.1 parts by weight of potassium persulfate, 0.01 parts by weight of ferric sulfate and about 0.1 parts by weight of an emulsifier, detergent soap are mixed then heated to 80° to 100° C. temperature while agitating at ambient pressure for 10 to 30 minutes thereby producing a cream colored emulsion of poly(methyl methacrylate silicate) resin, an acrylic silicate resinous product.

The acrylic silicate resinous product may be coagulated by slowly adding dilute acid, hydrochloric acid, until all the resin is coagulated. The emulsion of the acrylic silicate resinous product may also be poured into a dilute solution of hydrochloric acid and forms a solution. The unreacted silica may be precipitated and removed. The acrylic silicate resinous product may be coagulated from the hydrochloric acid by adjusting the pH to 6 to 8 with an alkali, such as sodium carbonate. It may also be coagulated with an alcohol such as methanol. The coagulated resinous product is soluble in acetone and isopropyl alcohol and may be molded into useful products by heat and pressure.

EXAMPLE V

About 2 parts by weight of fine granular silica, 2 parts by weight of acrylic acid, 0.5 parts by weight of sodium hydroxide flakes, 10 parts by weight of water, 0.005 to 0.02 parts by weight of potassium persulfate, and 0.01 to 0.005 parts by weight of ferric sulfate are mixed then heated to 80° to 100° C. while agitating for 10 to 30 minutes thereby producing an acrylic silicate resinous product, a cream colored aqueous emulsion.

The acrylic silicate resinous product is coagulated by slowly adding dilute hydrochloric acid until the pH is about 7. The acrylic silicate resinous product is not soluble in the usual acrylic resin solvents such as water, alcohol, acetic acid, sodium hydroxide aqueous solution, ammonium aqueous solution and acrylic acid.

It may be ground into a powder and molded into useful products by heat and pressure.

EXAMPLE VI

About 2 parts by weight of fine granular silica, 10 parts by weight of water, 0.75 parts by weight of sodium hydroxide flakes, 1 part by weight of methyl methacrylate, 1.5 parts by weight of acrylic acid, 0.01 to 0.02 parts by weight of potassium persulfate, 0.001 to 0.002 parts by weight of ferric sulfate and 0.02 parts by weight of an emulsifier, soap, are mixed then heated to 80° to 100° C. while agitating at ambient pressure for 10 to 30 minutes thereby producing a light gray acrylic silicate resinous product in an emulsion state.

The emulsion of the acrylic silicate resinous product is coagulated by addition of dilute acid, sulfuric acid, until the pH is about 7 to 8, thereby producing a solid white acrylic silicate resinous product.

EXAMPLE VII

About 2 parts by weight of fine granular silica, 10 parts by weight of water, 1 part by weight of sodium hydroxide, 2 parts by weight of methyl methacrylate, 0.01 parts by weight of potassium persulfate, 0.001 to 0.002 parts by weight of cupric sulfate and about 0.01 parts by weight of an emulsifier, soap, are mixed then heated to 80° to 100° C. while agitating at ambient pressure for 10 to 30 minutes thereby producing a light gray colored emulsion of an acrylic silicate resinous product.

About 30 parts by weight of water are slowly added to the emulsion while agitating then filtering the emulsion. About 0.5 parts by weight of the silica was filtered out unreacted. The emulsion of the acrylic silicate resinous product is coagulated by addition to a dilute acid until the pH is about 7 to 8 thereby producing a solid white acrylic silicate resinous product.

EXAMPLE VIII

About 2 parts by weight of fine granular silica, 0.5 parts by weight of potassium hydroxide pellets, 2.5 parts by weight of ethyl acrylic acid, 6 parts by weight of water, 0.02 parts by weight of ammonium persulfate, 0.001 parts by weight of ferric sulfate and 0.01 parts by weight of an emulsifier, sodium oleic acid soap are mixed then heated to 80° to 100° C. while agitating at ambient pressure for 10 to 30 munutes thereby producing a cream colored emulsion of an acrylic silicate resinous product.

EXAMPLE IX

About 2 parts by weight of a fine granular silica, 1 part by weight of potassium hydroxide, 10 parts by weight of water, 3 parts by weight of ethyl methacrylate, dodecyl mercaptan 0.01 parts by weight, 0.01 parts by weight of potassium persulfate, 0.5 parts by weight of anhydrous soap, 0.005 parts by weight of hydroquinone, and 0.05 parts by weight of phenyl $\beta$-naphthylamine are mixed then heated to 80° to 100° C. while agitating at ambient pressure for 10 to 30 minutes thereby producing a light gray colored emulsion of an acrylic resinous product.

EXAMPLE X

About 2 parts by weight of a fine granular silica, 1 part by weight of sodium hydroxide, 10 parts by weight of water, 1.5 parts by weight of methacrylic acid, 1.5 parts by weight of allyl methacrylate, 0.01 to 0.02 parts by weight of potassium persulfate, about 0.001 ferric sulfate, about 0.01 parts by weight of sodium palmate, are mixed then heated to 80° to 100° C. while agitating at ambient pressure for 10 to 30 minutes thereby producing an emulsion of an acrylic silicate resinous product.

EXAMPLE XI

About 2 parts by weight of a fine granular silica, 1.5 parts by weight of sodium hydroxide flakes, 15 parts by weight of water, 1.5 parts by weight of acrylic acid, 2 parts by weight of cyclohexyl-cyclohexyl methacrylate, 0.01 to 0.02 parts by weight of potassium persulfate, 0.001 parts by weight of ferric sulfate and 0.01 parts by weight of sodium myristic acid soap are mixed then heated to 80° to 100° C. while agitating at ambient pressure for 10 to 30 minutes thereby producing an emulsion of an acrylic silicate resinous product.

EXAMPLE XII

About 2 parts by weight of fine granular silica, 0.5 parts by weight of sodium hydroxide, 2 parts by weight of acrylic acid, 2 parts by weight of butadiene, 15 parts by weight of water, 0.05 parts by weight of soap, 0.005 to 0.01 parts by weight of ferric sulfate, 0.01 parts by weight of hydrogen peroxide and 0.01 parts by weight of lauryl mercaptan are mixed in a closed system at ambient temperature to 50° C. while agitating at about 40 to 60 psig for 30 to 120 minutes; then the mixture is heated to 80° to 100° C. at ambient pressure for 10 to 30 minutes thereby producing a cream colored emulsion of butadiene acrylic resinous product. The reaction is complete in 12 to 24 hours. The emulsion is coagulated by the addition of a dilute mineral acid or hydrogen containing acid salt, such as dilute sulfuric acid. The coagulated acrylic butadiene resinous product is washed with water to remove the salt then filtered. It may be molded into useful products by heat and pressure.

EXAMPLE XIII 2 parts by weight of fine granular silica, 1 part by weight of sodium hydroxide flakes, 2 parts by weight of acrylic acid, 2 parts by weight of vinyl chloride, 10 parts by weight of water, 0.01 to 0.02 parts by weight of potassium persulfate, 0.001 to 0.02 parts by weight of ferric sulfate and 0.02 to 0.03 parts by weight of an emulsifier, anhydrous soap, are mixed then agitated at ambient pressure and temperature to 30 to 120 minutes. The mixture is then heated to 80° to 100° C. at ambient pressure while agitating for 10 to 30 minutes, thereby producing a light gray emulsion of vinyl chloride acrylic silicate resinous product.

The emulsion may be coagulated by the addition of a dilute mineral acid or hydrogen containing acid salt. The coagulated vinyl chloride acrylic silicate resinous product may soften with heat and molded into useful products. The emulsion of vinyl chloride acrylic silicate resinous product may be painted on wood, concrete or metal and forms a hard, tough, protective coating.

EXAMPLE XIV

About 2 parts by weight of fine granular silica, 2 parts by weight of acrylic acid, 10 parts by weight of water, 0.1 parts by weight of soap, 0.01 parts by weight of potassium persulfate, and 0.001 parts by weight of cupric sulfate are mixed; then 2 parts by weight of granular calcium carbide are slowly added while agitating at ambient temperature and pressure for 30 to 120 minutes. The mixture is then heated to a temperature of 80° to 100° C. while agitating at ambient pressure for 10 to 30 minutes thereby producing a light gray emulsion of an acetylene acrylic silicate resinous product.

The acetylene acrylic silicate resinous product is coagulated by the addition of a dilute acid or hydrogen containing acid salt thereby producing a gray elastic acetylene acrylic silicate resinous product which can be molded by heat and pressure into useful products. The emulsion may be painted on wood, concrete, metal or wallboard to form a tough, protective coating.

EXAMPLE XV

About 2 parts by weight of fine granular silica, 1 part by weight of sodium hydroxide flakes, 2 parts by weight of acrylic acid, 15 parts by weight of water, 0.03 parts by weight of soap, 0.01 parts by weight of potassium persulfate and 0.001 parts by weight of ferric sulfate are mixed; then about 3 parts by weight of ethylene are slowly added while agitating in a closed system for 30 to 120 minutes at ambient pressure to 60 psig and ambient temperature. The mixture is then heated to 80° to 100° C. while agitating for 10 to 30 minutes thereby producing a cream colored emulsion of ethylene acrylic silicate resinous product.

The ethylene acrylic silicate resinous product may be coagulated from the emulsion by the addition of an acid or a hydrogen containing salt. The coagulated ethylene acrylic silicate resinous product may be molded into useful products by heat and pressure.

EXAMPLE XVI

About 2 parts by weight of fine granular silica, 0.5 parts by weight of sodium hydroxide flakes, 2 parts by weight of acrylic acid, 15 parts by weight of water, 0.05 parts by weight of soap, 0.01 parts by weight of potassium persulfate and 0.001 parts by weight of ferric sulfate are mixed; then about 2 parts by weight of propylene are slowly added while agitating at ambient pressure to 60 psig in a closed system at ambient temperature for 30 to 120 minutes. The mixture is then heated to a temperature of 80° to 100° C. while agitating at ambient pressure for 10 to 30 minutes thereby producing a cream colored emulsion of propylene acrylic silicate resinous product.

The propylene acrylic silicate resinous product is coagulated by the addition of a dilute acid or hydrogen containing salt thereby producing a cream colored propylene acrylic silicate resinous product. It may be molded into useful products by heat and pressure.

EXAMPLE XVII

About 2 parts by weight of silica, 1.5 parts by weight of acrylic acid, 2 parts by weight of 3-chloropropene, 1 part by weight of sodium hydroxide flakes, 15 parts by weight of water, 0.1 parts by weight of soap and 0.001 parts by weight of ferric sulfate are mixed then heated to 80° to 100° C. while agitating at ambient pressure for 10 to 30 minutes thereby producing a light gray colored emulsion of chloropropene acrylic silicate resinous product.

The chloropropene acrylic silicate resinous product is coagulated by the addition of a dilute acid or hydrogen containing salt thereby producing a light gray colored chloropropene acrylic silicate resinous product. It softens between 60° to 80° C. and may be molded into useful products.

EXAMPLE XVIII

About 2 parts by weight of fine granular silica, 1 part by weight of sodium hydroxide, 15 parts by weight of water, 2 parts by weight of acrylic acid, 2 parts by weight of isoprene, 0.01 parts by weight of soap, 0.01 parts by weight of potassium persulfate and 0.001 parts by weight of ferric sulfate are mixed then heated to 80° to 100° C. for 10 to 30 minutes at ambient pressure thereby producing a cream colored emulsion of isoprene acrylic silicate resinous product.

The isoprene acrylic silicate resinous product is soluble in dilute hydrochloric acid and is coagulated by the addition of an alkali such as sodium carbonate. The coagulated resinous product is elastic, and on drying, becomes a tough, solid product which softens at 80° to 110° C. and may be molded into useful products.

EXAMPLE XIX

About 2 parts by weight of fine granular silica, 1 part by weight of sodium hydroxide, 15 parts by weight of water, 2 parts by weight of acrylic acid, 4 parts by weight of acrylonitrile, 0.01 parts by weight of potassium persulfate and 0.001 parts by weight of ferric sulfate are mixed then heated to 80° to 100° C. for 10 to 30 minutes at ambient pressure thereby producing a light tan colored acrylonitrile acrylic silicate resinous product. The reaction is complete in 12 to 24 hours.

The emulsion may be coagulated with dilute acid or a hydrogen containing salt. The emulsion may be poured into dilute hydrochloric acid and the acrylonitrile acrylic silicate resinous product is soluble. It may be coagulated from the dilute hydrochloric acid by the addition of an alkali such as sodium carbonate and forms a rubbery resin which becomes a tough, solid, resinous product when dried. The resinous product softens at 60° to 80° and may be molded into useful products.

EXAMPLE XX

About 2 parts by weight of fine granular silica, 1 part by weight of sodium hydroxide flakes, 15 parts by weight of water, 2 parts by weight of styrene, 0.01 parts by weight of soap, 0.01 parts by weight of potassium persulfate and 0.001 parts by weight of ferric sulfate are mixed then agitated at 80° to 100° C. at ambient pressure for 10 to 30 minutes thereby producing a cream colored styrene acrylic silicate resinous product. The reaction is complete in 12 to 24 hours.

The resinous product may be coagulated with an acid or a hydrogen containing salt. The emulsion may be poured into a dilute hydrochloric acid and is soluble. It may be coagulated by the addition of an alakli such as sodium carbonate. The resinous product softens between 50° to 150° C. and may be molded into useful products.

EXAMPLE XXI

About 2 parts by weight of fine granular silica, 1 part by weight of sodium hydroxide flakes, 15 parts by weight of water, 2 parts by weight of vinyl acetate, 2 parts by weight of acrylic acid, 0.01 parts by weight of soap, 0.01 parts by weight of potassium persulfate and 0.001 parts by weight of ferric sulfate are mixed then agitated at 80° to 100° C. at ambient pressure for 10 to 30 minutes thereby producing a light reddish brown vinyl acetate acrylic silicate resinous product. The reaction is complete in 12 to 24 hours.

The resinous product may be coagulated from the emulsion by the addition of an acid or hydrogen containing salt. The emulsion may be poured into a dilute hydrochloric acid and is soluble. It may be coagulated by the addition of an alkali such as sodium carbonate. The resinous product softens between 60° to 80° C. and may be molded into useful products.

EXAMPLE XXII

About 2 parts by weight of fine granular silica, 2 parts by weight of sodium hydroxide, 15 parts by weight of water, 2 parts by weight of acrylic acid, 2 parts by weight of ethylene dichloride, 0.01 parts by weight of soap, 0.01 parts by weight of potassium persulfate and 0.001 parts by weight of ferric sulfate are mixed then agitated at 80° to 100° C. at ambient pressure for 10 to 30 minutes thereby producing a light tan colored emulsion of ethylene dichloride acrylic silicate resinous product.

The emulsion may be coagulated by the addition of an acid or hydrogen salt. The emulsion may be poured into dilute hydrochloric acid and is soluble. It may be coagulated by adding an alkali such as potassium carbonate. The dried powder resinous product softens at 50° to 100° C. and may be painted on wood, metal or concrete and forms a tough protective coating.

EXAMPLE XXIII

About 2 parts by weight of acrylic acid, about 6 parts by weight of water, 0.5 parts by weight of sodium hydroxide flakes, 0.01 parts by weight of potassium persulfate and 0.001 parts by weight of ferric sulfate are mixed and agitated for about 10 minutes at ambient pressure; then about 2 parts by weight of fine granular silica are added then heated to 80° to 100° C. for 10 to 30 minutes while agitating at ambient pressure thereby producing a cream colored emulsion of acrylic silicate resinous product.

The emulsion may be coagulated by the addition of an acid or hydrogen containing salt. The emulsion may be poured into dilute hydrochloric acid and is soluble. The resinous product may be coagulated by the addition of an alkali, such as sodium carbonate. The acrylic silicate resinous product will form a light gray emulsion in ammonium hydroxide aqueous solution. The emulsion may be painted on wood and forms a clear protective coating.

EXAMPLE XXIV

About 2 parts by weight of fine granular silica, 0.5 parts by weight of calcium hydroxide, 2 parts by weight of acrylic acid, 15 parts by weight of water, 0.01 parts by weight of potassium persulfate and 0.001 parts by weight of ferric sulfate are mixed then agitated at 80° to 100° C. at ambient pressure for 10 to 30 minutes thereby producing a white colored emulsion of acrylic silicate resinous product.

The emulsion of acrylic silicate resinous product is coagulated by adding dilute hydrochloric acid.

EXAMPLE XXV

About 2 parts by weight of a fine granular silica, 0.5 parts by weight of sodium hydroxide flakes, 2 parts by weight of acrylic acid, 15 parts by weight of water, 0.01 parts by weight of potassium persulfate, 0.01 parts by weight of soap, and 0.01 parts by weight of ferric sulfate are mixed, then 2 parts by weight of ethylene oxide are added slowly in a closed system under ambient temperature and pressure then agitated for 30 to 120 minutes. The mixture is then heated to 80° to 100° C. while agitating the ambient pressure for 10 to 30 minutes thereby producing an emulsion of ethylene oxide acrylic silicate resinous product.

The resinous product is coagulated from the emulsion by addition of an acid or hydrogen containing salt as sodium hydrogen sulfate. The resinous product will soften with heat and may be molded into useful products.

EXAMPLE XXVI

About 2 parts by weight of a fine granular silica, 0.5 parts by weight of acrylic acid, 1.5 parts by weight of methacrylic acid, 2 parts by weight of allyl alcohol, 15 parts by weight of water, 0.01 parts by weight of sodium alkyl sulfate, 0.01 to 0.02 parts by weight of ammonium persulfate, about 0.001 to 0.002 parts by weight of sodium thiosulfate are mixed then agitated at ambient pressure and temperature for 30 to 120 minutes. The mixture is then heated to 80° to 100° C. while agitating at ambient pressure for 10 to 30 minutes thereby producing a light gray colored emulsion of allyl alcohol acrylic silicate resinous product. The resinous product is soluble in hydrochloric acid and may be coagulated by the addition of an alkali compound such as sodium carbonate. The emulsion may be painted on wood and forms a tough protective coating. The coagulated resinous product may be molded into useful objects by heat and pressure.

Although specific conditions and ingredients have been described in conjunction with the above Examples of preferred embodiments, these may be varied, and other reagents and additives may be used, where suitable, as described above, with similar results.

Other modifications and applications of this invention will occur to those skilled in the art upon reading this disclosure. These are intended to be included with the scope of this invention, as defined in the appended claims.

I claim:

1. The process for the production of acrylic compounds and resinous products by the following steps:
    (a) mixing about 2 parts by weight of a fine granular silica with an acrylic compound in water;
    (b) adding 0.5 to 1.5 parts by weight of an alkali catalyst;
    (c) adding a catalytic amount of a peroxide initiator;
    (d) heating the said mixture to 80° to 100° C. while agitating for 10 to 30 minutes at ambient pressure, thereby
    (e) producing an emulsion of an acrylic silicate resinous product.

2. The process of claim 1 wherein the acrylic compound is selected from the group consisting of acrylic acid, methacrylic acid, ethyl acrylic acid, crotonic acid, chloroacrylic acid, fluoroacrylic acid, cyclohexyl methacrylic acid, isobutyl methacrylic acid, bromoacrylic acid, hydroacylic acid, benzyl acrylic acid and mixtures thereof.

3. The process of claim 1 wherein the acrylic compound is selected from the group consisting of ethyl acrylate, propyl acrylate, butyl acrylate, pentadecyl acrylate, hexadecyl acrylate, benzyl acrylate, cyclohexyl acrylate, phenyl ethyl acrylate, methyl methacrylate, ethyl methacrylate, methyl α-chloroacrylate, 2-chloroethyl acrylate, 1,1-dihydroperfluorobutyl acrylate, lauryl acrylate, cyclohexyl-cyclohexyl methacrylate, allyl methacrylate, ethylene methacrylate, n-butyl methacrylate, polyethylene glycol dimethacrylate, tetraethylene glycol dimethacrylate and mixtures thereof.

4. The process of claim 1 wherein the alkali catalyst is selected from alkali metal hydroxides consisting of sodium hydroxide and potassium hydroxide.

5. The process of claim 1 wherein the alkali catalyst is an alkaline earth metal hydroxide, calcium hydroxide.

6. The process of claim 1 wherein the peroxide initiator is selected from the group consisting of hydrogen peroxide, potassium persulfate, ammonium persulfate, cumene hydroperoxide, benzoyl peroxide, ethyl ketone peroxide with cobalt naphthenate, and o-menthane hydroperoxide.

7. The process of claim 1 wherein the peroxide initiator is potassium persulfate, 0.01 to 0.02 parts by weight, and ferric sulfate, 0.001 to 0.002 parts by weight.

8. The process of claim 1 wherein the peroxide initiator is utilized in a redox system, consisting of 10 to 15 parts by weight of water, 0.01 to 0.02 parts by weight of ammonium persulfate, about 0.001 to 0.002 parts by weight of cupric sulfate and about 0.01 to 0.02 parts by weight of sodium thiosulfate.

9. The process of claim 1 wherein an additional step of adding a dilute acid solution consisting of sulfuric acid, hydrochloric acid, acetic acid, sodium hydrogen sulfate to the emulsion of acrylic silicate resinous product until the pH is about 6 to 7 thereby coagulating the emulsion of acrylic silicate resinous product.

10. The process of claim 1 wherein an additional step is added in step (c) wherein 2 to 4 parts by weight of a vinyl monomer is selected from the group consisting of styrene, vinyl acetate, vinyl chloride, vinylidine chloride, acrylonitrile, vinyl toluenes, and mixtures thereof, is added while agitating at ambient pressure to 60 psig and a temperature of from ambient temperature to 50° C. for 30 to 120 minutes, thereby producing a vinyl acrylic silicate resinous product in step (e).

11. The process of claim 1 wherein an additional step is added in step (c) wherein 2 to 4 parts by weight of an aliphatic allyl compound, consisting of allyl alcohol and 3-chloropropene, is added and agitating at ambient temperature and pressure for 30 to 120 minutes thereby producing an allyl acrylic silicate resinous product in step (e).

12. The process of claim 1 wherein an additional step is added in step (c) wherein 2 to 4 parts by weight of an aliphatic dichloride selected from the group consisting of ethylene dichloride, bis(2-chloroethyl)ether, propylene dichloride and mixtures thereof, and agitated at ambient temperature and pressure for 30 to 120 minutes thereby producing an aliphatic acrylic silicate resinous product in step (e).

13. The process of claim 1 wherein an additional step is added in step (c) wherein 2 to 4 parts by weight of an organic oxide, selected from the group consisting of propylene oxide and ethylene oxide, is added slowly while agitating for 30 to 120 minutes in a closed system under ambient temperature and from ambient pressure to 60 psig, thereby producing an organic oxide acrylic silicate resinous product in step (e).

14. The process of claim 1 wherein an additional step is added in step (c) wherein 2 to 4 parts by weight of an organic diene compound, selected from the group consisting of isoprene, chloroprene and butadiene, is added then agitated in a closed system at ambient temperature to 50° C. temperature and from ambient pressure to 60 psig for 30 to 120 minutes thereby producing an organic diene acrylic silicate resinous product in step (e).

15. The process of claim 1 wherein an emulsifier is added in the amount of 0.01 to 0.05 parts by weight and selected from the group consisting of sodium alkyl sulfate compounds, and soaps.

16. The process of claim 1 wherein an acrylic acid compound is copolymerized with an acrylate compound.

17. The process of claim 1 wherein an additional step is added is step (c) wherein 2 to 4 parts by weight of an aliphatic hydrocarbon, selected from the group consisting of ethylene and propylene, is added then agitated at ambient temperature and at an ambient pressure to 60 psig for 30 to 120 minutes thereby producing an aliphatic acrylic silicate resinous product in step (e).

18. The product produced according to the process of claim 1.

* * * * *